(12) United States Patent
Satoh (10) Patent No.: US 7,696,251 B2
(45) Date of Patent: Apr. 13, 2010

(54) METHOD FOR INHIBITING NEURONAL CELL DEATH INDUCED BY OXIDATIVE GLUTAMATE TOXICITY

(75) Inventor: Takumi Satoh, Morioka (JP)

(73) Assignee: Incorporated National University Iwate University, Iwate (JP)

( * ) Notice: Subject to any disclaimer, the term of this patent is extended or adjusted under 35 U.S.C. 154(b) by 0 days.

(21) Appl. No.: 12/029,157

(22) Filed: Feb. 11, 2008

(65) Prior Publication Data

US 2008/0207765 A1 Aug. 28, 2008

Related U.S. Application Data

(60) Provisional application No. 60/889,473, filed on Feb. 12, 2007.

(51) Int. Cl.
*A61K 31/135* (2006.01)
*A61K 31/136* (2006.01)
(52) U.S. Cl. .................................................. 514/658
(58) Field of Classification Search ....................... None
See application file for complete search history.

(56) References Cited

U.S. PATENT DOCUMENTS

| | | | | |
|---|---|---|---|---|
| 6,231,852 B1* | 5/2001 | Bredesen | .................... | 424/94.4 |
| 6,746,678 B1* | 6/2004 | Shapiro | ....................... | 424/400 |
| 2005/0031651 A1* | 2/2005 | Gervais et al. | .............. | 424/400 |
| 2006/0160848 A1* | 7/2006 | Burcham et al. | ............ | 514/310 |
| 2007/0049576 A1* | 3/2007 | Barlow et al. | .......... | 514/214.03 |
| 2007/0122491 A1 | 5/2007 | Lyons et al. | | |
| 2007/0155687 A1 | 7/2007 | Lyons et al. | | |
| 2008/0004255 A1 | 1/2008 | Lyons et al. | | |
| 2008/0008692 A1* | 1/2008 | Lyons et al. | ............. | 424/93.51 |

FOREIGN PATENT DOCUMENTS

JP 2007-106732 4/2007

OTHER PUBLICATIONS

Miyamoto et al.: J Pharm Exp Therapeu, 250:1132-1140, 1989.*
Satoh et al.: Brain Research, 733:9-14, 1996.*
J.T. Coyle, P. Puttfarcken, Oxidative stress, glutamate and neurodegenerative disorders, Science 262 (1993) 689-695.
T. Satoh, S.A. Lipton, Redox regulation of neuronal survival by electrophilic compounds, Trends Neurosci. 30 (2007) 37-45.
T. Satoh, S. Okamoto, J. Cui, Y. Watanabe, K. Furuta, M. Suzuki, K. Tohyama, S.A. Lipton, Activation of the Keap1/Nrf2 pathway for neuroprotection by electrophilic phase II Inducers. Proc. Nat. Acad. Sci, USA 103 (2006) 768-773.
T. Satoh, Y. Enokido, K. Kubo, M. Yamada, H. Hatanaka, Oxygen toxicity induces apoptosis in neuronal cells, Cell. Mol. Neurobiol. 18 (1998) 649-666.
J.D. Butterfield, C.P. McGraw, Effect of DPPD (diphenyl-para-phenylenediamine) on stroke and cerebral edema in gerbils, Stroke 9 (1978) 480-483.

S.Y. Kim, C.H. Kim, H.J. Yoo, Y.K. Kim, Effects of radical scavengers and antioxidant on ischemic acute renal failure in rabbit, Ren. Fail. 21 (1999) 1-11.
G.D. Castro, A.J. Lopez, A.R. Petricio, J.A. Castro, Effect of the pretreatment with pyrazole, cystamine or diphenyl-P-phenylenediamine (DPPD) on the $CCl_4$-promoted pentane evolution in rats, Re. Comm. Chem. Pathol. Pharmacol. 52 (1986) 137-140.
E. Dickancaite, A. Nemeikaite, A. Kalvelyte, N. Cenas, Prooxidant character of flavonoid cytotoxicity: structure-activity relationships, Biochem. Mol. Biol. Int. 45 (1998) 923-930.
S.J. Robb, J.R. Connor, An in vitro model for analysis of oxidative death in primary mouse astrocytes, Brain Res. 788 (1998) 1225-132.
K. Ollinger, U.T. Brunk, Cellular injury induced by oxidative stress is mediated through lysozomal damage, Free Radic. Biol. Med. 19 (1995) 565-574.
B. van de Water, J.P. Zoeteweji, H.J. de Bont, J.F. Nagelkerke, Inhibition of succinate: ubiquinone reductase and decrease of ubiquinol in nephrotoxic cysteine S-conjugate-induced oxidative cell injury, Mol. Pharmacol. 48 (1995) 928-937.
I. Latour, J.B. Demoulin, P. Buc-Calderon, Oxidative DNA damage by t-butylhydroperoxide causes DNS single strand breaks which is not linked to cell lysis. A mechanistic study in freshly isolated rat hepatocytes, FEBS Lett. 373 (1995) 299-302.
H. Aoshima, T. Satoh, N. Sakai, M. Yamada, Y. Enokido, T. Ikeuchi, H. Hatanaka, Generation of free radicals during lipid hydroperoxide-triggered apoptosis in PC12 cells, Biophy. Biochem. Acta 1345 (1997) 35-42.
T. Satoh, N. Sakai, Y. Enokido, Y. Uchiyama, H. Hatanaka, Survival factor-insensitive generation of reactive oxygen species induced by serum deprivation in neuronal cells, Brain Res. 739 (1996) 9-14.
E.V. Berry, N.J. Toms, Pyruvate and oxalacetate limit zinc-induced oxidative HT-22 neuronal cell injury, Neurotoxicol. 27 (2006) 1043-1051.
J.B. Davis, P. Maher, Protein kinase C activation inhibits glutamate-induced cytotoxicity in a neuronal cell line, Brain Res. 652 (1994) 169-173.
Y. Sagara, K. Ishige, C. Tsai, P. Maher, Tyrphostins protect neuronal cells from oxidative stress, J. Biol. Chem. 277 (2002) 36204-36215.
T. Satoh, D, Nakatsuka, Y. Watanababe, N. Nagata, H. Kikuchi, S. Namura, Neuroprotection by MEK/ERK kinase inhibition with U0126 against oxidative stress in a mouse neuronal cell line and rat primary cultured neurons, Neurosci. Lett. 288 (2000) 163-166.

(Continued)

*Primary Examiner*—Brian-Yong S Kwon
*Assistant Examiner*—Bong-Sook Baek
(74) *Attorney, Agent, or Firm*—Ditthavong Mori & Steiner, P.C.

(57) ABSTRACT

A neuronal cell death induced by an oxidative glutamate toxicity is substantially inhibited by administrating to an mammal an effective amount of a phenylenediamine derivative compound of formula (I), wherein R is phenyl or butyl.

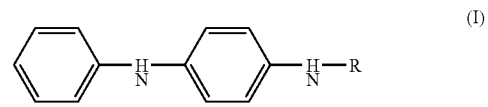

3 Claims, 5 Drawing Sheets

OTHER PUBLICATIONS

T. Satoh, K. Furuta, K. Tomokiyo, S. Namura, D. Nakatsuka, Y. Sugie, Y. Ishikawa, H. Hatanaka, M. Suzuki, Y. Watanabe, Neurotrophic actions of novel compounds designed from cyclopentenone prostaglandins, J. Neurochem. 77 (2001) 50-62.

S.J. Baker, E.P. Reddy, Modulation of life and death by TNF receptor superfamily. Oncogene 17 (1998) 3261-3270.

T. Satoh, K. Ishige, Y. Sagara, Protective effects on neuronal cells by ebselen against oxidative stress at multiple steps, Neurosci. Lett. 16 (2004) 1-5.

T. Satoh, T. Numakawa, Y. Abiru, T. Yamagata, Y. Ishikawa, Y. Enokido, H. Hatanaka, Production of reactive oxygen species and release of L-glutamate during superoxide anion-induced cell death of cerebellar granule neurons, J. Neurochem. 70 (1998) 316-324.

R. Dargusch, D. Schubert, Specificity of resistance to oxidative stress, J. Neurochem. 81 (2002) 1394-1400.

* cited by examiner

METHOD FOR INHIBITING NEURONAL CELL DEATH INDUCED BY OXIDATIVE GLUTAMATE TOXICITY

CROSS-REFERENCE TO RELATED APPLICATIONS

The present application claims priority under 35 U.S.C. §119(e) to Provisional Application No. 60/889,473, filed Feb. 12, 2007, entitled "Neuroprotective Effects of Phenylenediamine Derivatives Independent of an Antioxidant Pathway." The contents of this provisional application are incorporated herein by reference in their entirety.

BACKGROUND OF THE INVENTION

1. Field of the invention

The present invention relates to a method for inhibiting a neuronal cell death induced by oxidative glutamate toxicity.

2. Discussion of the Background

Resistance to oxidative stress often determines neuronal survival in the brain. Thus, antioxidants appear to be promising neuroprotective compounds against neurodegenerative diseases. For example, N,N'-diphenyl-p-phenylenediamine (DPPD) reportedly exerts cytoprotective effects against oxidative stress, possibly by acting as an antioxidant. DPPD provides hydrogen thereby scavenging free radicals, and protects cells from oxidative stress. However, there is no critical biological evidence to show that its antioxidant ability actually prevents cell death.

Oxidative stress, defined as the accumulation of reactive oxygen species (ROS) caused by enhancement of ROS production or by suppression of ROS destruction, plays a pivotal role in neurodegeneration associated with ischemia, trauma, and other neurodegenerative diseases [1-4]. The accumulation of ROS in neurons results in lipid peroxidation, protein oxidation, DNA damage, and finally cell death [1-4]. Thus, antioxidants are one of the potential targets of drug development for neuroprotection [2-3]. Basically, antioxidants are categorized into two distinctive groups: 1) hydrophilic and 2) lipophilic ones. Hydrophilic antioxidants, such as vitamin C or glutathione, are believed to react with water-soluble ROSs (superoxide anion [O2-], or hydrogen peroxide [H2O2]). In contrast, lipophilic antioxidants are believed to suppress lipid peroxidation. Two of the latter, vitamin E and N,N'-diphenyl-p-phenylenediamine (DPPD, FIG. 1) are believed to become inserted into the cell membrane and maintain membrane integrity, thereby providing potent cytoprotective actions against oxidative stress [1]. In vivo, DPPD protected animals against various insults initiated by oxidative stress resulting from brain or renal ischemia or carbon tetrachloride treatment [5-7]. Also, DPPD exerted a cytoprotective effects in vitro against oxidative stress on various types of cells including neuronal cell lines PC12 and HT22 [8-15]. For example, DPPD at μM concentrations protected PC12 cells against lipid peroxide, which protection was associated with a decrease in intracellular ROS levels [13]. These results suggest that DPPD protects neuronal cells against oxidative stress by acting as an antioxidant in both in vivo and in vitro systems [5-15].

There exists a need for methods of substantially inhibiting a neuronal cell death induced by an oxidative glutamate toxicity.

SUMMARY OF THE INVENTION

According to one aspect of the present invention, a neuronal cell death induced by an oxidative glutamate toxicity is substantially inhibited by administrating to an mammal an effective amount of a phenylenediamine derivative compound of formula (I), wherein R is phenyl or butyl.

(I)

BRIEF DESCRIPTION OF THE DRAWINGS

A more complete appreciation of the invention and many of its attendant advantages thereof will be readily obtained as the same becomes better understood by reference to the following detailed description when considered in connection with the accompanying drawings:

FIGS. 2A, 2B, and 2C show effects by DPPD on the cell death various stimuli;

DESCRIPTION OF THE EMBODIMENTS

Embodiments of the present invention will now be described with reference to the accompanying drawings, wherein like reference numerals designate corresponding or identical elements throughout the various drawings.

In accordance with embodiments of the present invention, DPPD as well as phenylenediamine derivatives are employed to inhibit cell death pathway independent of their antioxidant activity. It was found that DPPD inhibited the oxidative glutamate toxicity, but not substantially the tumor necrosis factor α-, hydrogen peroxide-, or xanthine+xanthine oxidase-induced death of HT22 cells, a mouse neuronal cell line. DPPD and phenylenediamine derivatives protected HT22 cells against oxidative glutamate toxicity at nM concentrations. By studying the structure-function relationship of these compounds, the structure of phenyl-amine-phenyl-amine-phenyl (or butyl) is believed to be essential for the neuroprotective effects. These results, as described below, suggest that DPPD inhibits an event in the death pathway initiated by glutamate, and that the neuroprotective effects were not due to its antioxidant capacity.

Abbreviations: AcD, actinomycin D; DMSO, dimethyl sulfoxide; DPPD, N,N'-Diphenyl-p-phenylenediamine; $H_2O_2$ hydrogen peroxide; MTT, 3-(4,5-dimethylthiazol-2-yl)-2,5-diphenyl tetrazolium bromide; $O_2$—, superoxide anion; ROS, reactive oxygen species; TNFα, tumor necrosis factor α; XA, xanthine; XO, xanthine oxidase. (YOSHI: ADD μM and nM definitions).

EXAMPLE

Experimentation was conducted to determine the cellular mechanism responsible for the neuroprotective effects of DPPD on cultured neuronal cells. It was found that a nM order of DPPD protected HT22 cells against oxidative glutamate toxicity, but not substantially against tumor necrosis factor α (TNFα)-, hydrogen peroxide ($H_2O_2$)—, or xanthine+xanthine oxidase (XA+XO)-induced cell death. These results indicate that nM order of DPPD does not substantially function as an antioxidant and that it may inhibit an event in the death pathway initiated by oxidative glutamate toxicity.

Figure 1:
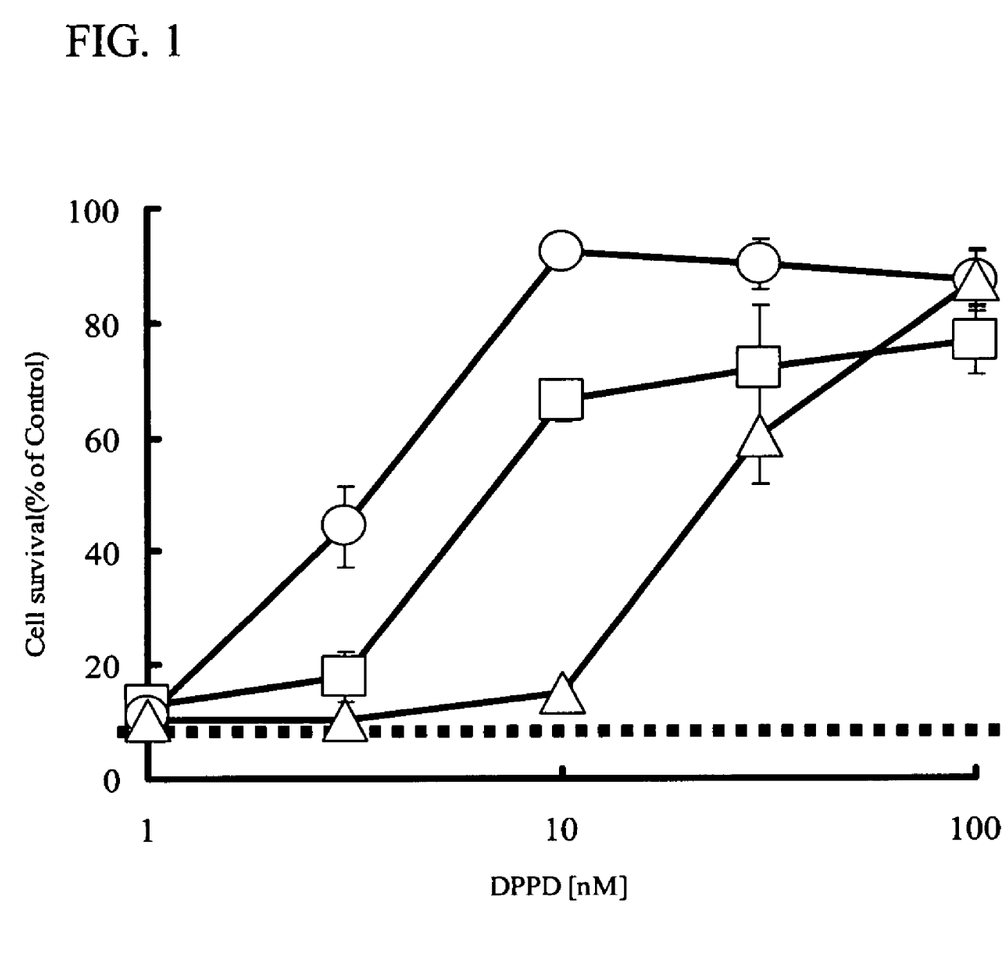
FIG. 1 shows a dose-response curve of neuroprotective effects by DPPD and its derivatives.

DPPD and its derivatives, shown in FIG. 1, were obtained from Ouchi Shinko Chemical Industrial (Tokyo, Japan). The compounds were dissolved in dimethyl sulfoxide (DMSO). The final concentration of DMSO in the culture medium was 0.1%. TNFα, actinomycin D (AcD), XA, XO, glutamate and $H_2O_2$ were purchased from Sigma (St. Louis, Mo., USA). HT22 cells [16-17] were cultured and MTT assays were performed as described previously [18-19]. Experiments presented here were repeated at least 3 times with 4 samples for each determination. The data are presented as the mean ±SD (for in vitro experiments). In order to examine the neuroprotective effects of DPPD, we employed the following 4 death-inducing agents: 1) glutamate (oxidative stress, transcription-dependent), 2) TNFα (receptor-mediated apoptosis, transcription-independent), 3) $H_2O_2$ (oxidative stress, transcription-independent) and 4) XA+XO (oxidative stress, transcription-independent). In FIG. 1, squares, DPPD; circles, D1; triangles, D2. The dotted line shows the level of cell survival in the absence of test compounds. HT22 cells were seeded into 24-well plates at a density of $4 \times 10^4$ cells/$cm^2$. After a 5-hr incubation, various concentrations of the compounds were added. One hour later, 5 mM of glutamate was added to the cultures, and 20 h thereafter, the cells were subjected to the MTT assay. The values, which represent the percentage of the control MTT activity, are means ±S.D.s (n=4).

DPPD and its derivatives were prepared as shown in Table 1. It has been reported that μM concentrations of DPPD reduced ROS levels and protected PC12 cells [13-14]. Interestingly, the results show that much lower concentrations (nM order) of DPPD protected the cells against oxidative glutamate toxicity (FIG. 1). By comparison of DPPD and its derivatives (D2-4), 2 compounds (DPPD and D1) had $IC_{50}$ lower than 10 nM (7.7 and 5.4 nM, respectively). D2 (phenyl-amine-phenyl) was slightly weaker $IC_{50}$ (26 nM). In contrast, D3 and D4 (amine-phenyl-amine, phenyl-amine, respectively) had much weaker neuroprotection (879 and 94000 nM, respectively). Thus, the common structure that had a potent neuroprotective effect was phenyl-amine-phenyl-amine-phenyl(butyl).

TABLE 1

Chemical structure of DPPD and its derivatives 1-4 (D1-4) and concentration of half inhibition ($IC_{50}$) of oxidative glutamate toxicity

| Abbreviation | Chemical name | $IC_{50}$ [nM] |
|---|---|---|
| DPPD | N,N-Diphenyl-p-phenylendiamine | 7.7 |
| D1 | N-Isopropyl-N-phenyl-phenylenediamine | 5.4 |
| D2 | 4-Aminodiphenylamine | 26 |
| D3 | Phenylene diamine | 879 |
| D4 | Aniline | 94000 |

Figure 2A:
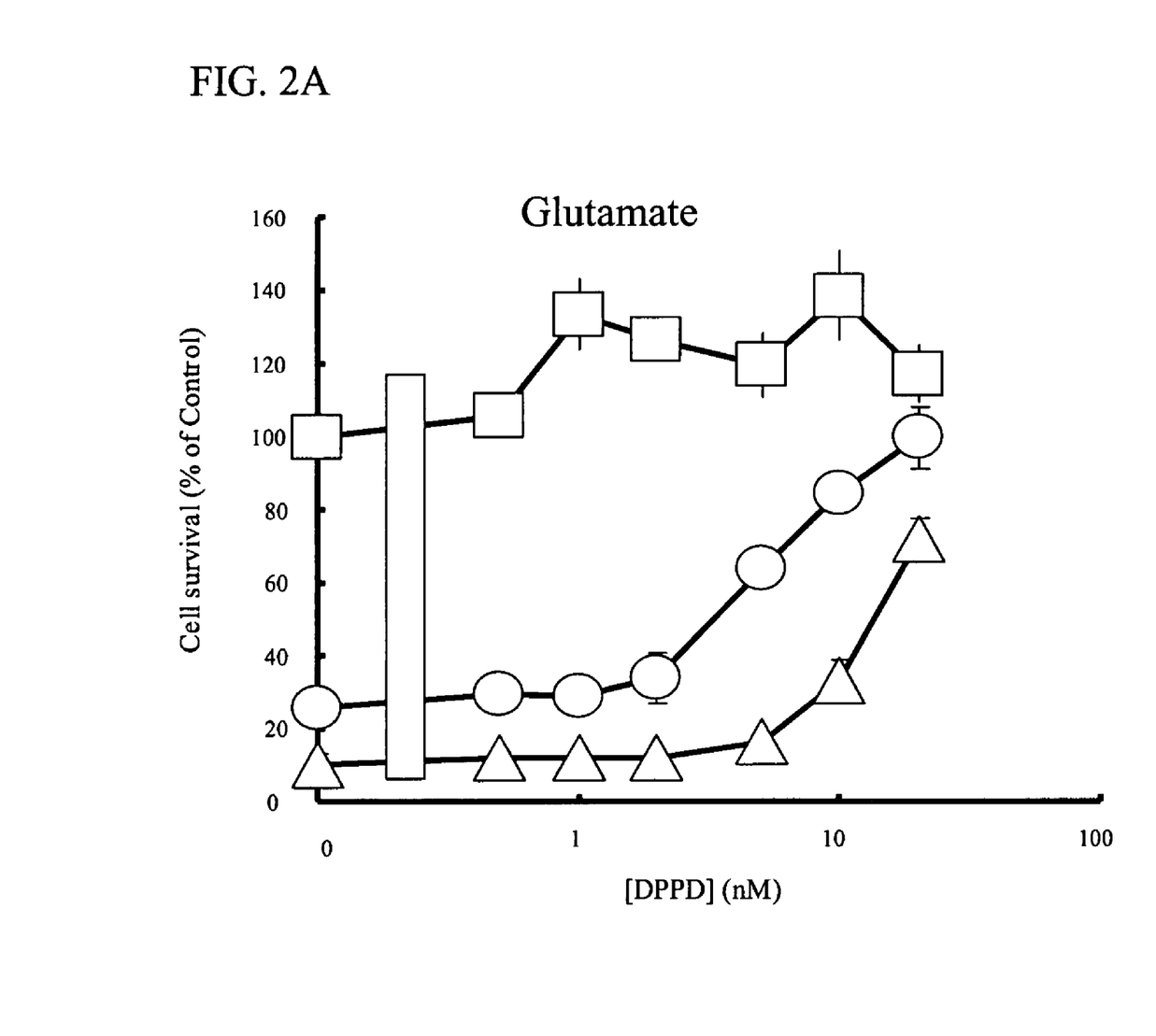
FIG. 2A shows the DPPD effect on the cell death induced by Glutamate. Squares, vehicle; circles, 5 mM glutamate; triangles, 10 mM glutamate.
Figure 2B:
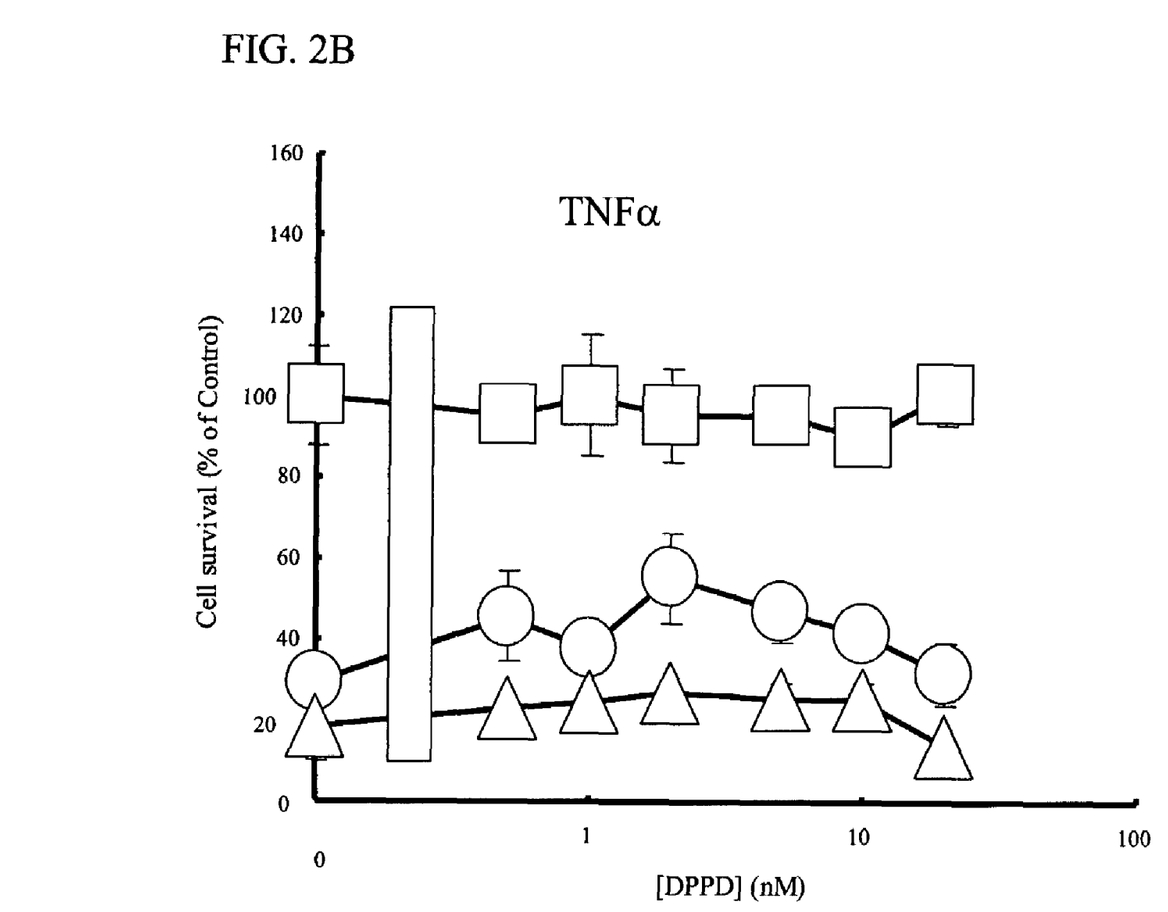
FIG. 2B shows the DPPD effect on the cell death induced by TNFα: Squares, vehicle; circles, 0.1 ng/ml TNFα; triangles, 1.0 ng/ml TNFα.
Figure 2C:
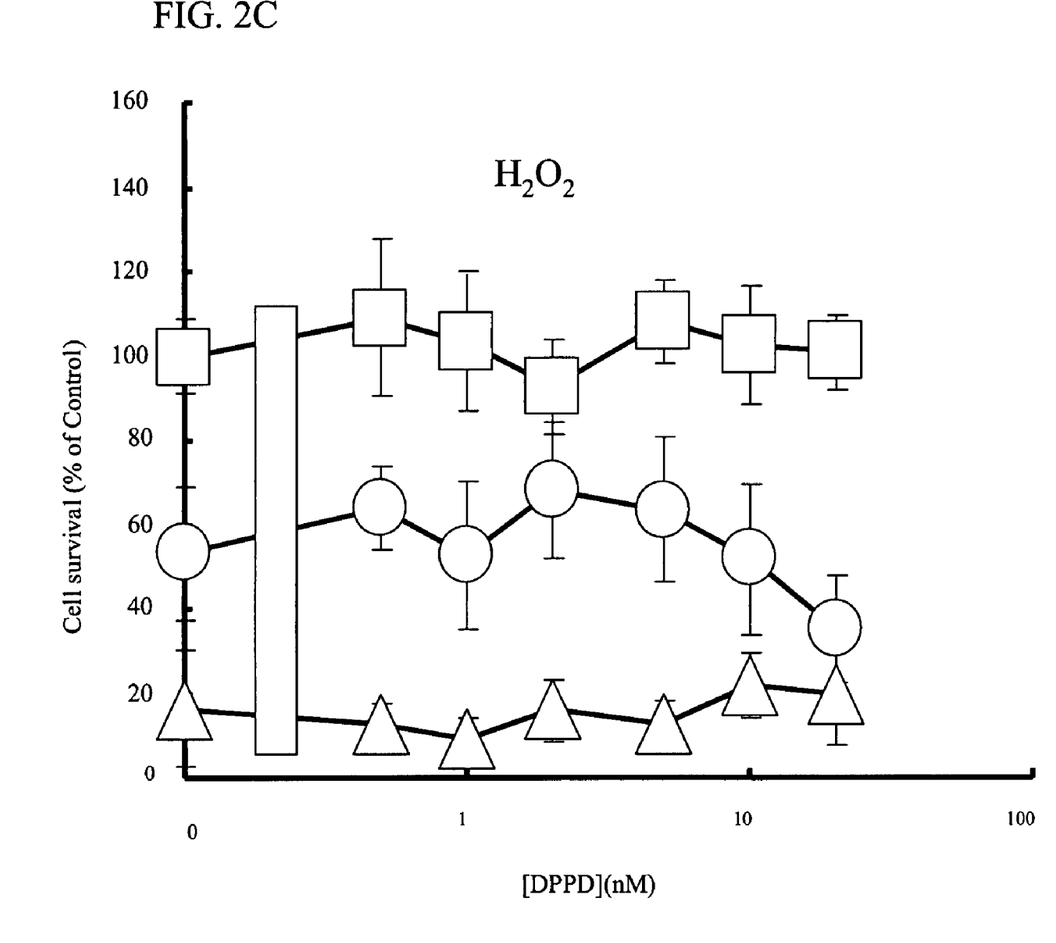
FIG. 2C shows the DPPD effect on the cell death induced by $H_2O_2$. Squares, vehicle; circles, 30 μM $H_2O_2$; triangles, 50 μM $H_2O_2$.
Figure 2D:
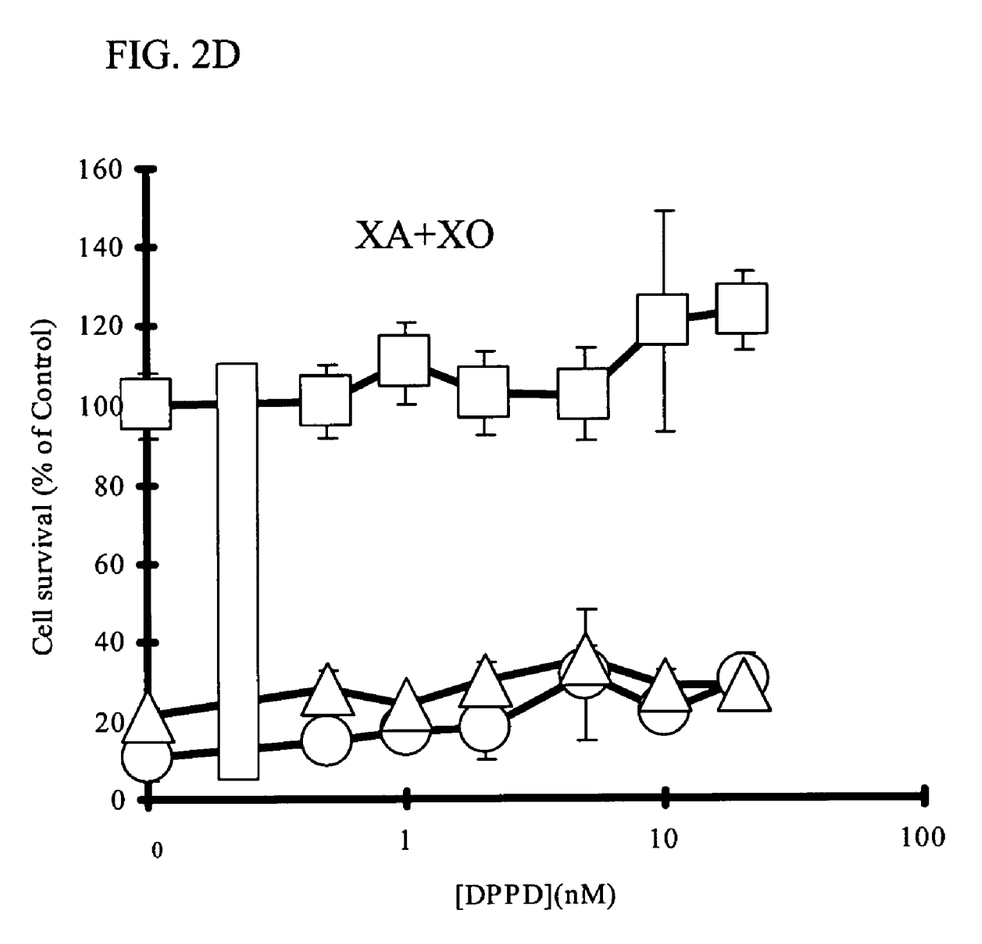
FIG. 2D shows the DPPD effect on the cell death induced by XA+XO. Squares, vehicle; circles, 15 mU/ml XO; triangles, 30 mU/ml XO.

In order to determine whether the inhibition was substantially specific to cell death by oxidative glutamate toxicity, the effects of these compounds on the cell death induced by various stimuli were examined. Adverting to FIGS. 2A, 2B, 2C and 2D, 2HT22 cells were seeded into 24-well plates at a density of $4 \times 10^4$ cells/$cm^2$. After a 5-hr incubation, various concentrations of DPPD were added. One hour later, the cells were treated for 20 h with glutamate (A), TNFα in the presence of 0.1 μg/ml AcD (B), $H_2O_2$ (C) and XO in the presence of 0.1 mg/ml of XA (D) and then were subjected to the MTT assay. The values, which represent the percentage of the control MTT activity, are means ±S.D.s (n=4). It was found that DPPD at 1-10 nM almost completely blocked the death of HT22 cells induced by 5 or 10 mM glutamate (FIG. 2A), but was substantially ineffective against the TNFα-induced neuronal death (FIG. 2B). Furthermore, DPPD did not substantially protect HT22 cells against $H_2O_2$— or XA+XO-induced cell death (FIGS. 2C and D). These results are in a sharp contrast to those on ebselen, a typical antioxidant, which prevented the death induced by glutamate or $H_2O_2$ but not that induced by TNFα [20].

DPPD has been widely employed in biological experiments as an antioxidant, and has been reported to decrease ROS levels when used at µM order concentrations [13-14]. However, the neuroprotective effects shown in the present study cannot be due to its antioxidant activities in light of the following three findings: 1) DPPD did not substantially prevent the $H_2O_2$-induced cell death; 2) DPPD did not substantially prevent the XA+XO-induced cell death; and 3) DPPD protected the glutamate-treated cells at nM concentrations, which were about 1000 fold lower than those effective to decrease ROS levels.

FIG. 2B showed DPPD to be substantially ineffective against TNFα-induced cell death. The TNFα receptor proteins appear to transmit their signals via protein-protein interactions between death domain-integrated proteins, and the death signals seem to be associated with the activation of both caspase and JUN kinase pathways [20]. TNFα induces apoptosis of HT22 cells in the presence of AcD [21]. TNFα-induced death occurs by typical apoptosis and is substantially distinct from that induced by oxidative glutamate toxicity. In HT22 cells, ROS-scavenging molecules such as ebselen could not substantially inhibit the death induced by TNFα [21]. As reported earlier, XA+XO induced an increase in $O_2^-$ and $H_2O_2$ levels in granular neurons of cerebellum and the actual cause of death was the accumulation of $H_2O_2$, based on the findings that catalase, not SOD, prevented the XA+XO-induced neuronal death [22]. The common feature of death induced by $H_2O_2$ and XA+XO is the induction by ROS themselves. Thus, the mechanism of the protective effect of HT22 cells against oxidative glutamate toxicity dose not appear to be due to the decrease in ROS levels. Since the oxidative glutamate toxicity requires multiple steps leading to accumulation of ROS [23], it is concluded that DPPD inhibited an intracellular event of the pathway from glutamate to cell death. Dursgush and Schubert assumed that cell death induced by oxidative glutamate toxicity is distinct from both apoptosis and necrosis, and suggest that it should called as oxytosis [23]. The most distinctive aspect of the mechanism of oxytosis is the involvement of transcription, i.e. oxytosis, but substantially not death induced by TNFα, $H_2O_2$ and XA+XO, requiring the transcription of certain genes [23]. Thus, DPPD appears to inhibit the induction of death-inducing genes and/or activate death-inhibiting genes.

The contents of the references below are incorporated herein by reference in their entirety.

REFERENCES

[1] J. T. Coyle, P. Puttfarcken, Oxidative stress, glutamate and neurodegenerative disorders, Science 262 (1993) 689-695.

[2] T. Satoh, S. A. Lipton, Redox regulation of neuronal survival by electrophilic compounds, Trends Neurosci. 30 (2007) 37-45.

[3] T. Satoh, S. Okamoto, J. Cui, Y. Watanabe, K. Furuta, M. Suzuki, K. Tohyama, S. A. Lipton, Activation of the Keap1/Nrf2 pathway for neuroprotection by electrophilic phase II Inducers. Proc. Nat. Acad. Sci, USA 103 (2006) 768-773.

[4] T. Satoh, Y. Enokido, K. Kubo, M. Yamada, H. Hatanaka, Oxygen toxicity induces apoptosis in neuronal cells, Cell. Mol. Neurobiol. 18 (1999) 649-666.

[5] J. D. Butterfield, C. P. McGraw, Effect of DPPD (diphenyl-para-phenylenediamine) on stroke and cerebral edema in gerbils, Stroke 9 (1978) 480-483.

[6] S. Y. Kim, C. H. Kim, H. J. Yoo, Y. K. Kim, Effects of radical scavengers and antioxidant on ischemic acute renal failure in rabbit, Ren. Fail. 21 (1999) 1-11.

[7] G. D. Castro, A. J. Lopez, A. R. Petricio, J. A. Castro, Effect of the pretreatment with pyrazole, cystamine or diphenyl-P-phenylenediamine (DPPD) on the $CCl_4$-promoted pentane evolution in rats, Re. Comm. Chem. Pathol. Pharmacol. 52 (1986) 137-140.

[8] E. Dickancaite, A. Nemeikaite, A. Kalvelyte, N. Cenas, Prooxidant character of flavonoid cytotoxicity: structure-activity relationships, Biochem. Mol. Biol. Int. 45 (1998) 923-930.

[9] S. J. Robb, J. R. Connor, An in vitro model for analysis of oxidative death in primary mouse astrocytes, Brain Res. 788 (1998) 1225-132.

[10] K. Ollinger, U. T. Brunk, Cellular injury induced by oxidative stress is mediated through lysozomal damage, Free Radic. Biol. Med. 19 (1995) 565-574.

[11] B. van de Water, J. P. Zoeteweji, H. J. de Bont, J. F. Nagelkerke, Inhibition of succinate: ubiquinone reductase and decrease of ubiquinol in nephrotoxic cysteine S-conjugate-induced oxidative cell injury, Mol. Pharmacol. 48 (1995) 928-937.

[12] I. Latour, J. B. Demoulin, P. BucCalderon, Oxidative DNA damage by t-butylhydroperoxide causes DNS single strand breaks which is not linked to cell lysis. A mechanistic study in freshly isolated rat hepatocytes, FEBS Lett. 373 (1995) 299-302.

[13] H. Aoshima, T. Satoh, N. Sakai, M. Yamada, Y. Enokido, T. Ikeuchi, H. Hatanaka, Generation of free radicals during lipid hydroperoxide-triggered apoptosis in PC12 cells, Biophy. Biochem. Acta 1345 (1997) 35-42.

[14] T. Satoh, N. Sakai, Y. Enokido, Y. Uchiyama, H. Hatanaka, Survival factor-insensitive generation of reactive oxygen species induced by serum deprivation in neuronal cells, Brain Res. 739 (1996) 9-14.

[15] B. V. Elizabeth, N. J. Toms, Pyruvate and oxalacetate limit zinc-induced oxidative HT-22 neuronal cell injury, Neurotoxicol. 27 (2006) 1043-1051.

[16] J. B. Davis, P. Maher, Protein kinase C activation inhibits glutamate-induced cytotoxicity in a neuronal cell line, Brain Res. 652 (1994) 169-173.

[17] Y. Sagara, K. Ishige, C. Tsai, P. Maher, Tyrphostins protect neuronal cells from oxidative stress, J. Biol. Chem. 277 (2002) 36204-36215

[18] T. Satoh, D, Nakatsuka, Y. Watanababe, N. Nagata, H. Kikuchi, S, Namura, Neuroprotection by MEK/ERK kinase inhibition against oxidative stress in a mouse neuronal cell line and rat primary cultured neurons, Neurosci. Lett. 288 (2000) 163-166.

[19] T. Satoh, K. Furuta, K. Tomokiyo, S, Namura, D. Nakatsuka, Y. Sugie, Y. Ishikawa, H. Hatanaka, M. Suzuki, Y. Watanabe, Neurotrophic actions of novel compounds designed from cyclopentenone prostaglandins, J. Neurochem. 77 (2001) 50-62.

[20] S. J. Baker, E. P. Reddy, Modulation of life and death by TNF receptor superfamily. Oncogene 17 (1998) 3261-3270.

[21] T. Satoh, K. Ishige, Y. Sagara, Protective effects on neuronal cells by ebselen against oxidative stress at multiple steps, Neurosci. Lett. 16 (2004) 1-5.

[22] T. Satoh, T. Numakawa, Y. Abiru, T. Yamagata, Y. Ishikawa, Y. Enokido, H. Hatanaka, Production of reactive oxygen species and release of L-glutamate during superoxide anion-induced cell death of cerebellar granule neurons, J. Neurocher. 70 (1998) 316-324.

[23] R. Dargusch, D. Schubert, Specificity of resistance to oxidative stress, J. Neurochem. 81 (2002) 1394-1400.

[24] Japanese Unexamined Patent Application Publication No. 2007-106732, U.S. Provisional Patent Applications No. USP 60/727,015, No. 60/727,018, and No. 60/726,951.

While the invention has been described in connection with a number of embodiments and implementations, the invention is not so limited but covers various obvious modifications and equivalent arrangements, which fall within the purview of the appended claims. Although features of the invention are expressed in certain combinations among the claims, it is contemplated that these features can be arranged in any combination and order.

What is claimed as new and is desired to be secured by Letters Patent of the United States is:

1. A method of reducing a neuronal cell death induced by an oxidative glutamate toxicity, the method comprising administrating to an mammal an effective amount from 1 to 100 nM of a phenylenediamine compound of formula (I), wherein R is isopropyl 2. The method according to claim 1, wherein an effective amount the phenylenediamine compound has 5.4 nM of $IC_{50}$ against an oxidative glutamate toxicity.

3. The method according to claim 1, wherein said effective amount of the phenylenediamine compound ranges from 1 to 10 nM.

* * * * *